US011389458B2

(12) United States Patent
Wang et al.

(10) Patent No.: US 11,389,458 B2
(45) Date of Patent: *Jul. 19, 2022

(54) PHARMACEUTICAL COMPOSITIONS AND METHODS FOR TREATING PARKINSON'S AND HUNTINGTON'S DISEASE

(71) Applicant: LA PharmaTech Inc., Blacksburg, VA (US)

(72) Inventors: Jianmin Wang, Blacksburg, VA (US); Geping Cui, Beijing (CN)

(73) Assignee: LA PharmaTech Inc., Blacksburg, VA (US)

( * ) Notice: Subject to any disclaimer, the term of this patent is extended or adjusted under 35 U.S.C. 154(b) by 141 days.

This patent is subject to a terminal disclaimer.

(21) Appl. No.: 16/834,146

(22) Filed: Mar. 30, 2020

(65) Prior Publication Data

US 2020/0323871 A1    Oct. 15, 2020

Related U.S. Application Data

(63) Continuation-in-part of application No. 16/426,121, filed on May 30, 2019, now Pat. No. 10,639,316, and a continuation-in-part of application No. 16/424,788, filed on May 29, 2019, now Pat. No. 10,946,026, and a continuation of application No. 16/418,614, filed on May 21, 2019, now Pat. No. 10,639,315, and a continuation of application No. PCT/US2019/033359, filed on May 21, 2019, said application No. 16/426,121 is a continuation of application No. 16/398,845, filed on Apr. 30, 2019, now Pat. No. 10,639,314, application No. 16/834,146, which is a continuation-in-part of application No. PCT/US2019/029885, filed on Apr. 30, 2019, said application No. 16/424,788 is a continuation of application No. 16/382,885, filed on Apr. 12, 2019, now Pat. No. 10,966,989, application No. 16/834,146, which is a continuation-in-part of application No. PCT/US2019/027293, filed on Apr. 12, 2019.

(51) Int. Cl.
| | |
|---|---|
| *A61K 31/55* | (2006.01) |
| *A61K 9/00* | (2006.01) |
| *A61P 25/28* | (2006.01) |
| *A61K 31/445* | (2006.01) |
| *A61K 31/165* | (2006.01) |

(52) U.S. Cl.
CPC ............ *A61K 31/55* (2013.01); *A61K 9/0053* (2013.01); *A61K 31/165* (2013.01); *A61K 31/445* (2013.01); *A61P 25/28* (2018.01)

(58) Field of Classification Search
CPC .... A61K 31/55; A61K 31/445; A61K 31/165; A61P 25/28
See application file for complete search history.

(56) References Cited

U.S. PATENT DOCUMENTS

| | | | |
|---|---|---|---|
| 5,068,233 | A | 11/1991 | Achterrath-Tuckerman et al. |
| 5,086,050 | A | 2/1992 | Hettche et al. |
| 5,110,814 | A | 5/1992 | Engel et al. |
| 5,994,357 | A | 11/1999 | Theoharides |
| 6,017,909 | A | 1/2000 | Hettche et al. |
| 6,849,621 | B2 | 2/2005 | Rosenblum et al. |
| 7,022,687 | B1 | 4/2006 | Szelenyi et al. |
| 7,220,735 | B2 | 5/2007 | Ting et al. |
| 7,355,042 | B2 | 4/2008 | Edgar et al. |
| 7,615,550 | B2 | 11/2009 | Heightman et al. |
| 7,786,161 | B2 | 8/2010 | Tani et al. |
| 8,071,073 | B2 | 12/2011 | Dang et al. |
| 8,168,620 | B2 | 5/2012 | Lulla et al. |
| 8,304,405 | B2 | 11/2012 | Lulla et al. |
| 8,318,709 | B2 | 11/2012 | Lulla et al. |
| 8,518,919 | B2 | 8/2013 | Dang et al. |
| 8,741,319 | B2 | 6/2014 | Crain et al. |
| 8,758,816 | B2 | 6/2014 | Fuge et al. |
| 8,859,531 | B2 | 10/2014 | Lee et al. |
| 8,865,733 | B2 | 10/2014 | Felder |
| 9,278,092 | B2 | 3/2016 | Chase et al. |
| 9,901,585 | B2 | 2/2018 | Lulla et al. |
| 9,919,050 | B2 | 3/2018 | Dang et al. |
| 10,639,314 | B1 | 5/2020 | Wang et al. |
| 10,639,315 | B1 | 5/2020 | Wang et al. |

(Continued)

FOREIGN PATENT DOCUMENTS

| | | |
|---|---|---|
| AU | 2019443520 A1 | 12/2021 |
| AU | 2019445048 A1 | 12/2021 |

(Continued)

OTHER PUBLICATIONS

Exelon Highlights of Prescribing Information (Novartis Pharmaceuticals Corporation, Revised Jan. 2015, 24 pages) (Year: 2015).*
Memantine and Donepezil Hydrochlorides Extended-Release Capsules (Amneal Pharmaceuticals, Revised Oct. 2016, 31 pages) (Year: 2016).*
(Wang, Jianmin) Co-Pending U.S. Appl. No. 16/382,885, filed Apr. 12, 2019, Specification and claims.
(Wang, Jianmin) Co-Pending U.S. Appl. No. 16/398,845, filed Apr. 30, 2019, Specification and Claims.

(Continued)

*Primary Examiner* — James D. Anderson
(74) *Attorney, Agent, or Firm* — New River Valley IP Law, PC; Michele L. Mayberry

(57) ABSTRACT

A pharmaceutical composition containing the therapeutically active ingredients of azelastine or a pharmaceutically acceptable salt of azelastine and donepezil or rivastigmine or galantamine or a pharmaceutically acceptable salt of thereof is disclosed. A method of using the pharmaceutical composition for treating patients suffering from mental, behavioral, cognitive disorders is also disclosed.

18 Claims, No Drawings

(56) References Cited

U.S. PATENT DOCUMENTS

| | | | |
|---|---|---|---|
| 10,639,316 | B1 | 5/2020 | Wang et al. |
| 10,898,493 | B2 | 1/2021 | Wang et al. |
| 10,946,026 | B2 * | 3/2021 | Wang ..................... A61P 25/28 |
| 10,966,989 | B2 | 4/2021 | Wang et al. |
| 11,116,773 | B2 * | 9/2021 | Wang ..................... A61K 31/55 |
| 11,318,144 | B2 | 5/2022 | Wang et al. |
| 2003/0229030 | A1 | 12/2003 | Theoharides |
| 2005/0163843 | A1 | 7/2005 | Boehm et al. |
| 2006/0051416 | A1 | 3/2006 | Rastogi et al. |
| 2009/0318703 | A1 | 12/2009 | Tani et al. |
| 2010/0152108 | A1 | 6/2010 | Hung et al. |
| 2012/0237570 | A1 | 9/2012 | Crain et al. |
| 2013/0252929 | A1 | 9/2013 | Lee et al. |
| 2014/0158117 | A1 | 6/2014 | Dang et al. |
| 2015/0216849 | A1 | 8/2015 | Dedhiya et al. |
| 2017/0035780 | A1 | 2/2017 | Lulla et al. |
| 2018/0104294 | A1 | 4/2018 | Vuckovic |
| 2018/0116979 | A1 | 5/2018 | Clarence-Smith et al. |
| 2020/0323867 | A1 | 10/2020 | Wang et al. |
| 2020/0323868 | A1 | 10/2020 | Wang et al. |
| 2020/0323870 | A1 | 10/2020 | Wang et al. |
| 2020/0323873 | A1 | 10/2020 | Wang et al. |
| 2020/0323876 | A1 | 10/2020 | Wang et al. |
| 2020/0323877 | A1 | 10/2020 | Wang et al. |
| 2021/0069209 | A1 | 3/2021 | Wang et al. |
| 2022/0000882 | A1 | 1/2022 | Wang et al. |
| 2022/0096491 | A1 | 3/2022 | Wang et al. |

FOREIGN PATENT DOCUMENTS

| | | | |
|---|---|---|---|
| AU | 2019446955 | A1 | 12/2021 |
| CA | 3136633 | A1 | 10/2020 |
| CA | 3137393 | A1 | 11/2020 |
| CA | 3139082 | A1 | 11/2020 |
| CN | 113924098 | A | 1/2022 |
| CN | 113939276 | A | 1/2022 |
| EP | 3952840 | A1 | 2/2022 |
| WO | 2006058022 | A1 | 6/2006 |
| WO | 2007061454 | A1 | 5/2007 |
| WO | 2014018563 | A3 | 5/2014 |
| WO | 2020209872 | A1 | 10/2020 |
| WO | 2020222799 | A1 | 11/2020 |
| WO | 2020236159 | A1 | 11/2020 |
| WO | 2021242235 | A1 | 12/2021 |
| WO | 2021242297 | A1 | 12/2021 |
| WO | 2021262196 | A1 | 12/2021 |

OTHER PUBLICATIONS (Wang, Jianmin) Co-Pending U.S. Appl. No. 16/418,614, filed May 21, 2019, Specification and Claims.
(Wang, Jianmin) Co-pending U.S. Appl. No. 16/424,788, filed May 29, 2019, Specification and Claims.
(Wang, Jianmin) Co-Pending U.S. Appl. No. 16/426,121, filed May 30, 2019, Specification and Claims.
(Wang, Jianmin) Co-Pending U.S. Appl. No. 16/831,330, filed Mar. 26, 2020, Specification and Claims.
(Wang, Jianmin) Co-Pending U.S. Appl. No. 16/884,459, filed May 27, 2020, Specification and Claims.
(Wang, Jianmin) Co-Pending U.S. Appl. No. 16/884,553, filed May 27, 2020, Specification and Claims.
(Wang, Jianmin) Co-Pending U.S. Appl. No. 16/913,927, filed Jun. 26, 2020, Specification and Claims.
(Wang, Jianmin) Co-Pending Application No. PCT/US19/29885, Filed Apr. 30, 2019, Specification and Claims.
(Wang, Jianmin) Co-Pending Application No. PCT/US19/33359, Filed May 21, 2019, Specification and Claims.
(Wang, Jianmin) Co-Pending Application No. PCT/US20/39916, Filed Jun. 26, 2020, Specification and Claims.
(Wang, Jianmin) Co-Pending Application No. PCT/US2019/027293, filed Apr. 12, 2019, Specification and Claims.
Aricept, Generic Name: donepezil hydrochloride, Brand Name: Aricept, Drug Description, RxList.com, Jan. 3, 2019.
Bezprozvanny, Ilya. The rise and fall of Dimebon. National Institute of Health. Feb. 12, 2014.
Casale, T. B. The interaction of azelastine with human lung histamine H1, beta, and muscarinic receptor-binding sites. J Allergy Clin Immunol 1989;83:771-776.
Category H1 receptor antagonists. Wikipedia. Sep. 20, 2012.
Ciprandi, G., Pronzato, C., Passalacqua, G., et al. Topical azelastine reduces eosinophil activation and intercellular adhesion molecule-1 expression on nasal epithelial cells: An antiallergic activity. J Allergy Clin Immunol. 1996;98(6 Pt 1): 1088-1096.
Co-Pending U.S. Appl. No. 16/382,885, Final office action dated Jun. 5, 2020, 13 pgs.
Co-Pending U.S. Appl. No. 16/382,885, Non-Final office action and list of references dated Nov. 29, 2019, 23 pgs.
Co-Pending U.S. Appl. No. 16/382,885, Response dated Nov. 29, 2019 Non-Final office action filed Mar. 2, 2020.
Co-Pending U.S. Appl. No. 16/382,885, Response to restriction requirement dated Oct. 2, 2019, 3pgs.
Co-Pending U.S. Appl. No. 16/382,885, Restriction Requirement dated Aug. 9, 2019, 7 pgs.
Co-Pending U.S. Appl. No. 16/398,845, Interview Summary dated Dec. 18, 2019, 7 pages.
Co-Pending U.S. Appl. No. 16/398,845, Non-Final Office Action dated Aug. 6, 2019, 25 pages.
Co-Pending U.S. Appl. No. 16/398,845, Notice of Allowance dated Jan. 21, 2020, 11 pages.
Co-Pending U.S. Appl. No. 16/398,845, Response to Non-Final Office Action dated Nov. 3, 2019, 9 pages.
Co-Pending U.S. Appl. No. 16/418,614, Interview Summary dated Dec. 18, 2019, 7 pages.
Co-Pending U.S. Appl. No. 16/418,614, Non-Final Office Action dated Aug. 6, 2019, 31 pages.
Co-Pending U.S. Appl. No. 16/418,614, Notice of Allowance dated Jan. 30, 2020, 12 pages.
Co-Pending U.S. Appl. No. 16/418,614, Response to Non-Final Office Action dated Nov. 3, 2019, 10 pages.
Co-Pending U.S. Appl. No. 16/424,788 Non-Final Office Action, dated Nov. 29, 2019, 24 pgs.
Co-Pending U.S. Appl. No. 16/424,788 Response dated Nov. 29, 2019 Non-Final Office Action, filed Mar. 2, 2020.
Co-Pending U.S. Appl. No. 16/424,788 Response to Restriction Requirement, dated Oct. 2, 2019, 3 pgs.
Co-Pending U.S. Appl. No. 16/424,788 Restriction Requirement, dated Aug. 9, 2019, 7 ogs.
Co-Pending U.S. Appl. No. 16/426,121, Non-Final Office Action dated Aug. 6, 2019, 25 pages.
Co-Pending U.S. Appl. No. 16/426,121, Notice of allowance dated Jan. 21, 2020, 18 pages.
Co-Pending U.S. Appl. No. 16/426,121, Response to Non-Final Office Action dated Nov. 6, 2019, 9 pages.
Co-Pending application No. PCT/US19/29885 International Search Report dated Jul. 15, 2019 7 pages.
Co-Pending application No. PCT/US19/33359 International Search Report and Written Opinior dated Aug. 15, 2019. 9 pages.
Co-Pending Application No. PCT/US2019/027293, Search Report & Written Opinion, dated Sep. 17, 2019, 8 pages.
Goedert, M., Spillantini, M.G,. 2006. A century of Alzheimer's disease. Science, 314:777-81.
Hansen et al. Clinical Interventions in Aging 2008, vol. 3, No. 2, pp. 211-225.
Hatakeyama, AikO, Masahiko Fujii, Reiko Hatakeyama, Yumiko Fukuoka, Takuma Satoh-Nakagawa and Hidetada Sasaki, Azelastine hydrochloride on behavioral and psychological symptoms and activities of daily living in dementia patients, Geriatr Gerontol Int 2008; 8: 59-61 (2008).
Hazama, H., Nakajima, T., Hisada, T., Hamada, E., Omata, M., Kurachi, Y. Effects of azelastine on membrane currents in tracheal smooth muscle cells isolated from the guinea-pig. Eur J Pharmacol. 1994;259: 143-150.
Kempuraj, Duraisamy, et al. 2003, Azelastine Inhibits Secretion of IL-6, TNF-alpha and IL-8 as Well as NF-kappaB Activation and Intracellular Calcium Ion Levels in Normal Human Mast Cells. Int Arch Allergy Immunol. 132 (3), 231-9 Nov. 2003.

(56) References Cited

OTHER PUBLICATIONS

Naddafi, F., Mirshafiey A., The neglected role of histamine in Alzheimer's disease., Jun. 2013;28(4):327-36. doi: 10.1177/1533317513488925. Epub May 15, 2013.
Riethmuller et al. Arzneimittel-Forschung, 1994, vol. 44, No. 10, pp. 1136-1140.
Sedeyn, Jonathan Histamine Induces Alzheimer's Disease-Like Blood Brain Barrier Breach and local cellular Responses in Mouse Brain Organotypic Culture. Hindawi. Aug. 21, 2015.
Simons, F.E., Simons, K.J. Clinical pharmacology of new histamine H1 receptor antagonist. Clin Pharmacokinet. 1999;36:329-352.
St-Jean, Genevieve; Turcotte, Isabelle; Bastien, Celyne H. Cerebral asymmetry in insomnia sufferers. Frontiers in Neurology 2012, 3, 1-12.
Szelenyi, I., Achterrath-Tuckermann, U., Schmidt, J., Minker, E., Paegelow, I., Werner, H. Azelastine: A multifaceted drug for asthma therapy. Agents Actions Suppl. 1991 ;34:295-311. (abstract).
Tanaka, Hibiki, Hashimoto, Mamoru, et al, 2015. Relationship Between Dementia Severity and Behavioural and Psychological Symptoms in Early-Onset Alzheimer's Disease. Psychogeriatrics. Dec. 2015;15(4):242-7.
Williams, Patricia B, Crandall, Elizabeth, and Sheppard, John D, 2010, Azelastine hydrochloride, a dual-acting anti-inflammatory ophthalmic solution, for treatment of allergic conjunctivitis. Clinical Ophthalmology 2010:4 993-1001.
Yoneda, Kazunori, et al. 1997, Suppression by Azelastine Hydrochloride of NF-KB Activation Involved in Generation of Cytokines and Nitric Oxide Japanese Journal of Pharmacology, 73: 145-53.
Co-Pending U.S. Appl. No. 16/382,885, Response dated Jun. 5, 2020 Final office action filed Jul. 31, 2020, 9 pages.
(Wang, Jianmin) Co-Pending U.S. Appl. No. 17/094,405, filed Nov. 10, 2020, Specification and Claims.
(Wang, Jianmin) Co-Pending U.S. Appl. No. 17/394,898, filed Aug. 5, 2021, Specification and Claims.
(Wang, Jianmin) Co-Pending U.S. Appl. No. 17/459,868, filed Aug. 27, 2021, Specification and Claims.
(Wang, Jianmin) Co-Pending U.S. Appl. No. 17/546,342, filed Dec. 9, 2021, Specification and Claims.
(Wang, Jianmin) Co-Pending U.S. Appl. No. 17/673,136, filed Feb. 16, 2022, Specification and Claims.
(Wang, Jianmin) Co-Pending Application No. PCT/US20/34735, filed May 27, 2020, Specification and Claims.
(Wang, Jianmin) Co-Pending Application No. PCT/US20/59846, filed Nov. 10, 2020, Specification and claims.
(Wang, Jianmin) Co-Pending Application No. PCT/US21/44654, filed Aug. 5, 2021, Specification and Claims.
(Wang, Jianmin) Co-Pending Application No. PCT/US22/16545, filed Feb. 16, 2022, Specification and Claims.
(Wang, Jianmin) Co-Pending Australia National Stage Application No. 2019443520, Effective Filing Date Apr. 30, 2019, Specification and Claims (See PCT/US19/29885, which published as WO 2020/222799, for Specification and Claims as filed).
(Wang, Jianmin) Co-Pending Australia National Stage Application No. 2019445048, Effective Filing Date Apr. 12, 2019, Specification and Claims (See PCT/US19/27293, which published as WO 2020/209872, for Specification and Claims as filed).
(Wang, Jianmin) Co-Pending Australia National Stage Application No. 2019446955, Effective Filing Date May 21, 2019, Specification and Claims (See PCT/US19/33359, which published as WO2020/236159, for Specification and Claims as filed).
(Wang, Jianmin) Co-Pending Canada National Stage Application No. 3,136,633, filed Oct. 3, 2021, Specification and Claims, 25 pages.
(Wang, Jianmin) Co-Pending Canada National Stage Application No. 3,137,393, Filed Oct. 19, 2021, Specification and Claims, 17 pages.
(Wang, Jianmin) Co-Pending Canada National Stage Application No. 3,139,082, Filed Nov. 3, 2021, Claims and Amended Specification, 25 pages.
(Wang, Jianmin) Co-Pending China National Stage Application No. 201980095322.X, filed Oct. 11, 2021, Specification and Claims (32 pages) (see PCT/US19/27293, which published as WO2020/209872 for English Translation).
(Wang, Jianmin) Co-Pending China National Stage Application No. 201980095741.3, Filed Oct. 25, 2021, Specification and Amended Claims as filed (26 pages) with English Translation of the Amended Claims (2 pages) (See PCT/US19/29885, which published as WO 2020/222799, for English Translation of the Specification).
(Wang, Jianmin) Co-Pending China National Stage Application No. 201980096574.4, Filed Nov. 18, 2021, Specification and Amended Claims as filed (48 pages) with English Translation of the Amended Claims (4 pages) (See PCT/US19/33359, which published as WO2020/236159, for English Translation of the Specification).
(Wang, Jianmin) Co-Pending European National Stage Application No. 19924315.5, filed Nov. 11, 2021, Specification and Amended Claims as filed (34 pages).
(Wang, Jianmin) Co-Pending European National Stage Application No. 19927207.1, filed Nov. 29, 2021, Specification and Amended Claims as filed (26 pages).
(Wang, Jianmin) Co-Pending European National Stage Application No. 19929933.0, filed Dec. 21, 2021, Specification and Amended Claims as filed (35 pages).
(Wang, Jianmin) Co-Pending Japan National Stage Application No. 2021-556914, filed Sep. 17, 2021, Specification and Claims (19 pages) (see PCT/US19/27293, which published as WO 2020/209872, for English Translation).
(Wang, Jianmin) Co-Pending Japan National Stage Application No. 2021-558496, filed Sep. 21, 2021, Specification and Claims (15 pages) (See PCT/US19/29885, which published as WO 2020/222799, for English Translation).
(Wang, Jianmin) Co-Pending Japan National Stage Application No. 2021-566489, filed Nov. 9, 2021, Request for Entry and Specification and Claims (18 pages) (See PCT/US19/33359, which published as WO2020/236159, for English Translation of Specification and Claims).
Co-Pending U.S. Appl. No. 16/382,885, Non-Final office action dated Dec. 22, 2020, 19 pgs.
Co-Pending U.S. Appl. No. 16/382,885, Notice of Allowance dated Feb. 10, 2021, 9 pages.
Co-Pending U.S. Appl. No. 16/382,885, Response dated Dec. 22, 2020 Non-Final office action filed Jan. 21, 2021, 7 pgs.
Co-Pending U.S. Appl. No. 16/424,788 Corrected Notice of Allowance, dated Jan. 7, 2021, 5 pages.
Co-Pending U.S. Appl. No. 16/424,788 Non-Final Office Action, dated Nov. 5, 2020, 8 pgs.
Co-Pending U.S. Appl. No. 16/424,788 Notice of Allowance, dated Dec. 17, 2020, 9 pages.
Co-Pending U.S. Appl. No. 16/424,788 Response dated Nov. 5, 2020 Non-Final Office Action, dated Dec. 2, 2020, 6 pages.
Co-Pending U.S. Appl. No. 16/424,788, Final Office Action dated Aug. 28, 2020, 17 pages.
Co-Pending U.S. Appl. No. 16/424,788, Response dated Aug. 28, 2020 Final Office Action filed Oct. 19, 2020, 6 pages.
Co-Pending U.S. Appl. No. 16/426,121, Interview Summary dated Dec. 18, 2019, 7 pages.
Co-Pending U.S. Appl. No. 16/831,330, Non-Final Office Action dated Apr. 7, 2021, 16 pages.
Co-Pending U.S. Appl. No. 16/831,330, Notice of Allowance dated Aug. 3, 2021, 8 pages.
Co-Pending U.S. Appl. No. 16/831,330, Response dated Apr. 7, 2021 Non-Final Office Action filed Jul. 21, 2021, 7 pages.
Co-Pending U.S. Appl. No. 16/884,459, Dec. 15, 2020 Final Office Action, 15 pages.
Co-Pending U.S. Appl. No. 16/884,459, Final Office Action dated Dec. 10, 2021, 19 pages.
Co-Pending U.S. Appl. No. 16/884,459, Non-Final Office Action dated Aug. 11, 2020, 35 pages.
Co-Pending U.S. Appl. No. 16/884,459, Non-Final Office Action dated Sep. 14, 2021, 35 pages.
Co-Pending U.S. Appl. No. 16/884,459, Response dated Aug. 11, 2020 Non-Final Office Action dated Nov. 12, 2020, 11 pages.

(56) References Cited

OTHER PUBLICATIONS

Co-Pending U.S. Appl. No. 16/884,459, Response dated Dec. 15, 2020 Final Office Action, filed Mar. 15, 2021, 30 pages.
Co-Pending U.S. Appl. No. 16/884,459, Response dated Sep. 14, 2021 Non-Final Office Action, filed Nov. 16, 2021, 9 pages.
Co-Pending U.S. Appl. No. 16/884,553, Non-Final Office Action dated Aug. 11, 2020, 26 pages.
Co-Pending U.S. Appl. No. 16/884,553, Notice of Allowance dated Dec. 2, 2020, 9 pages.
Co-Pending U.S. Appl. No. 16/884,553, Response dated Aug. 11, 2020 Non-Final Office Action dated Nov. 12, 2020, 8 pages.
Co-Pending U.S. Appl. No. 16/913,927, Final Office Action dated Dec. 3, 2021, 12 pages.
Co-Pending U.S. Appl. No. 16/913,927, Final Office Action dated Jun. 2, 2021, 16 pages.
Co-Pending U.S. Appl. No. 16/913,927, Non-Final Office Action dated Aug. 11, 2021, 17 pages.
Co-Pending U.S. Appl. No. 16/913,927, Non-Final Office Action dated Feb. 19, 2021, 19 pages.
Co-Pending U.S. Appl. No. 16/913,927, Non-Final Office Action dated Nov. 9, 2020, 24 pages.
Co-Pending U.S. Appl. No. 16/913,927, Response dated Aug. 11, 2021 Non-Final Office Action, dated Nov. 10, 2021, 6 pages.
Co-Pending U.S. Appl. No. 16/913,927, Response dated Aug. 27, 2020 Restriction Requirement, filed Oct. 20, 2020, 5 pages.
Co-Pending U.S. Appl. No. 16/913,927, Response dated Feb. 19, 2021 Non-Final Office Action filed May 19, 2021, 10 pages.
Co-Pending U.S. Appl. No. 16/913,927, Response dated Jun. 2, 2021 Final Office Action, dated Jul. 30, 2021, 6 pages.
Co-Pending U.S. Appl. No. 16/913,927, Response dated Nov. 9, 2020 Non-Final Office Action filed Feb. 5, 2021, 8 pages.
Co-Pending U.S. Appl. No. 16/913,927, Restriction Requirement dated Aug. 27, 2020, 5 pages.
Co-Pending U.S. Appl. No. 17/094,405, Final Office Action dated Jul. 30, 2021, 22 pages.
Co-Pending U.S. Appl. No. 17/094,405, Non-Final Office Action dated Apr. 14, 2021, 21 pages.
Co-Pending U.S. Appl. No. 17/094,405, Response dated Apr. 14, 2021 Non-Final Office Action filed Jul. 14, 2021, 7 pages.
Co-Pending U.S. Appl. No. 17/094,405, Response dated Jan. 26, 2021 Restriction Requirement, filed Apr. 5, 2021, 7 pages.
Co-Pending U.S. Appl. No. 17/094,405, Response dated Jul. 30, 2021 Final Office Action, dated Sep. 30, 2021, 10 pages.
Co-Pending U.S. Appl. No. 17/094,405, Restriction Requirement dated Jan. 26, 2021, 5 pages.
Co-Pending U.S. Appl. No. 17/394,898, Non-Final Office Action dated Nov. 24, 2021, 9 pages.
Co-Pending U.S. Appl. No. 17/394,898, Response dated Oct. 21, 2021 Restriction Requirement, dated Nov. 10, 2021, 2 pages.
Co-Pending U.S. Appl. No. 17/394,898, Restriction Requirement dated Oct. 21, 2021, 9 pages.
Co-Pending U.S. Appl. No. 17/459,868, Preliminary Amendment, filed Aug. 27, 2021, 8 pages.
Co-Pending Application No. PCT/US20/34735, International Search Report and Written Opinion dated Aug. 17, 2020, 10 pages.
Co-Pending Application No. PCT/US20/39916, International Search Report and Written Opinion dated Oct. 8, 2020, 8 pages.
Co-Pending Application No. PCT/US20/59846, International Search Report and Written Opinion dated Mar. 8, 2021, 8 pages.
Co-Pending Application No. PCT/US2019/027293, Corrected Written Opinion, dated Oct. 29, 2019, 5 pages.
Co-Pending Application No. PCT/US21/44654, International Search Report and Written Dpinion, dated Nov. 15, 2021, 10 pages.
Co-Pending China National Stage Application No. 201980095322.X, English Version of Amended Claims as filed Oct. 11, 2021, 3 pages.
Cummings et al. "Effect of Dextromethorphan-Quinidine on Agitation in Patients with Alzheimer Disease Dimentia: A Randomized Clinical Trial". JAMA, 2015; 314(12):1242-1254.
EHealthMe.com "Azelastine and Xanax drug interactions—a phase IV clinical study of FDA data", dated Jan. 7, 2021, 5 pages.
Galatowicz, G, Ajayi Y, Stern ME, Calder VL. Ocular antiallergic compounds selectively inhibit human mast cell cytokines in vitro and conjunctival cell infiltration in vivo. Clin Exp Allergy. 2007; 37:1648-1656.
Hashiro et al. "A Combination Therapy of Psychotropic Drugs and Antihistaminics or Antiallergics in Patients with Chronic Urticaria". Journal of Dermatological Sciences, 1996; 11:209-213.
Horak, Friedrich, "Effectiveness of twice daily azelastine nasal spray in patients with seasonal allergic rhinitis," Ther. Clin Risk Manag., Oct. 2008; 4(5): 1009-1022.
Hua, S. "Advances in Nanoparticulate Drug Delivery Approaches for Sublingual and Buccal Administration". Nov. 10, 2019 (Article 1328), pp. 1-9.
Munoz-Cano et al. "Severity of Allergic Rhinitis Impacts Sleep and Anxiety: Results from a Large Spanish Cohort". Clinical and Translational Allergy, 2018, 8 (Article 23), p. 1-9.
Starkstein, et al., "The construct of generalized anxiety disorder in altheimer's disease," Am J Geriatr Psychiatry Jan. 2007. 15(1) 42-49.
Co-Pending U.S. Appl. No. 17/094,405, Non-Final Office Action dated Apr. 14, 2022, 38 pages.
Co-Pending U.S. Appl. No. 17/673,136 Restriction Requirement dated May 3, 2022, 5 pages.
Co-Pending Application No. PCT/US22/16545 Invitation to Pay Fees dated Apr. 19, 2022, 2 pages.
Co-Pending Japan National Stage Application No. 2021-556914 Voluntary Amendment and Request for Exam dated Apr. 11, 2022, JP version (5 pages) and English (3 pages).
Co-Pending Japan National Stage Application No. 2021-558496 Voluntary Amendment and equest for Exam dated Apr. 14, 2022, JP version (4 pgs) and Englsh (2 pgs).
Co-Pending Japan National Stage Application No. 2021-566489 Voluntary Amendment and Request for Exam dated May 17, 2022, JP version (5 pgs) and English (4 pgs).

* cited by examiner

PHARMACEUTICAL COMPOSITIONS AND METHODS FOR TREATING PARKINSON'S AND HUNTINGTON'S DISEASE

CROSS-REFERENCE TO RELATED APPLICATIONS

The present application is a Continuation application of U.S. patent application Ser. No. 16/418,614 filed May 21, 2019, and is a Continuation-in-Part application of U.S. patent application Ser. No. 16/426,121 filed May 30, 2019, and is a Continuation-in-Part application of U.S. patent application Ser. No. 16/424,788 filed May 29, 2019. The '121 application is a Continuation application of U.S. patent application Ser. No. 16/398,845 filed Apr. 30, 2019. The '788 application is a Continuation application of U.S. patent application Ser. No. 16/382,885 filed Apr. 12, 2019. The present application is a Continuation application of International Application No. PCT/US19/33359 filed May 21, 2019, and is a Continuation-in-Part application of International Application No. PCT/US19/29885 filed Apr. 30, 2019, and is a Continuation-in-Part application of International Application No. PCT/US19/27293 filed Apr. 12, 2019. All of the foregoing applications are hereby incorporated herein by reference in their entireties.

FIELD OF THE INVENTION

The invention relates to the field of practical medicine, namely, to the combined use of pharmaceutical compositions exhibiting a neurotropic action, alleviating manifestations of mental, behavioral, cognitive disorders in cases of organic damage of various origin to the central nervous system.

BACKGROUND OF THE INVENTION

Alzheimer's disease (AD) is a progressive, chronic neurodegenerative disease that usually starts slowly and gradually worsens over time. Alzheimer's disease is the most common cause of dementia among older adults. Dementia is the loss of cognitive functioning—thinking, remembering, and reasoning—and behavioral abilities to such an extent that it interferes with a person's daily life and activities. In its early stages, memory loss is mild, but with late-stage AD, individuals lose the ability to carry on a conversation and respond to their environment. If untreated, AD ultimately leads to death. Although the speed of progression can vary, the typical life expectancy following diagnosis is three to nine years.

AD is a polygenic/multifactorial complex disorder characterized by the premature death of neurons. Although the amyloid hypothesis is recognized as the Primum Movens of AD pathogenesis, mutational genetics associated with amyloid precursor protein (APP) and presenilin (PS) genes lone does not explain in full the neuropathologic findings present in AD, represented by amyloid deposition in senile plaques and vessels (amyloid angiopathy), neurofibrillary tangle (NFT) formation due to hyperphosphorylation of tau protein, synaptic and dendritic desarborization and neuronal loss. These findings are companied by neuroinflammatory reactions, oxidative stress, and free radical formation probably associated with mitochondrial dysfunction, excitotoxic reactions, alterations in cholesterol metabolism and lipid rafts, deficiencies in neurotransmitters (especially acetylcholine) and neurotrophic factor function, defective activity of the ubiquitin-proteasome, and chaperone systems and cerebrovascular dysregulation. All these neurochemical events are potential targets for treatment; however, it is very unlikely that a single drug be able alone to neutralize the complex mechanisms involved in neurodegeneration.

In the early 1980s it was believed that AD-related memory dysfunction was in part due to a cholinergic deficit in the brain of affected people due to a loss of neurons in the basal forebrain, this giving rise to the cholinergic hypothesis of AD. Since choline donors (precursors) and acetylcholine itself were substances of difficult pharmacological management (or useless to increase brain cholinergic neurotransmission), and, paradoxically, considering that acetylcholinesterase activity progressively decreased in AD brains in parallel with cognitive deterioration, AChEIs were proposed as an option to inhibit acetylcholine degradation in the synaptic cleft and to increase choline reuptake at the presynaptic level with the aim of enhancing acetylcholine synthesis in presynaptic terminals, this facilitating cholinergic neurotransmission. The first candidate to fulfil this criteria was tacrine (tetrahydroaminoacridine) which after its introduction in the market in 1993 soon fell out of favor due to its hepatotoxicity and poor tolerability; 3 years later, in 1996, donepezil was approved by the FDA for the treatment of mild-to-moderate cases of AD. The other AChEIs, rivastigmine and galantamine, were introduced several years later.

However, acetylcholinesterase inhibitors such as donepezil, rivastigmine and galantamine will not cure AD or prevent the loss of these abilities at some time in the future. So AD has no current cure, and our effort is to find better ways to reverse the disease, delay and prevent it from developing.

On the other hand, the genetic, cellular, and molecular changes associated with AD support the evidence that activated immune and inflammatory processes is a part of the disease. Also a strong benefit of long-term use of NSAIDs was shown in epidemiological studies. So it is generally accepted that AD is partially an inflammatory disease and that inhibiting inflammation is an option of treating AD.

Inflammation clearly occurs in pathologically vulnerable regions of the AD brain, and it does so with the full complexity of local peripheral inflammatory responses. In the periphery, degenerating tissue and the deposition of highly insoluble abnormal materials are classical stimulants of inflammation. Likewise, in the AD brain damaged neurons and neurites and highly insoluble amyloid β peptide deposits and neurofibrillary tangles provide obvious stimuli for inflammation. Because these stimuli are discrete, micro-localized, and present from early preclinical to terminal stages of AD, local upregulation of complement, cytokines, acute phase reactants, and other inflammatory mediators is also discrete, micro-localized, and chronic. Cumulated over many years, direct and bystander damage from AD inflammatory mechanisms is likely to significantly exacerbate the very pathogenic processes that gave rise to it. Thus, animal models and clinical studies so far strongly suggest that AD inflammation significantly contributes to AD pathogenesis. By better understanding AD inflammatory and immune-regulatory processes, it should be possible to develop anti-inflammatory approaches that may reverse or delay or prevent developing of this devastating disorder.

Azelastine is classified pharmacologically as a second generation antihistamine and is a relatively selective, nonsedating, competitive antagonist at H1 receptors. More uniquely, its inhibition of inflammatory mediators, in addition to antihistaminic and mast cell stabilizing effects, places it among the new generation of dual-acting anti-inflammatory drugs. Its ability to modify several other mediators of inflammation and allergy contributes to its mechanism of action. In vitro and in vivo studies, as well as clinical trials support the dual effects of direct inhibition and stabilization of inflammatory cells. In vitro data indicate that azelastine's affinity for inhibition of mast cell degranulation may also decrease the release of other inflammatory mediators, including leukotrienes and interleukin-1β, among others. Azelastine also directly antagonizes other mediators of inflammation, such as tumor necrosis factor-α, leukotrienes, endothelin-1, and platelet-activating factor. Therefore, a unique combination of azelastine and donepezil and/or rivastigmine and/or galantamine is expected to be, in terms of creating synergistic effects, innovative potential treatments for AD.

SUMMARY OF THE INVENTION

The present invention includes a pharmaceutical composition that comprises two active ingredients and one or more pharmaceutically acceptable excipients. This pharmaceutical composition comprises the first active ingredient that is azelastine or a pharmaceutically acceptable salt of azelastine and the second active ingredient that is donepezil and/or rivastigmine and/or galantamine and/or any pharmaceutically acceptable salt thereof.

Included in embodiments of the invention is use of a composition comprising (i) azelastine or a pharmaceutically acceptable salt of azelastine, (ii) donepezil or rivastigmine or galantamine, or pharmaceutically acceptable salts thereof, or any combination thereof, and (iii) one or more pharmaceutically acceptable excipients for the treatment of one or more mental, behavioral, or cognitive disorder, such as Alzheimer's disease, vascular dementia, Parkinson's disease, Huntington's disease, or any combination thereof.

Also included within the scope of the invention is use of a composition comprising (i) azelastine or a pharmaceutically acceptable salt of azelastine, (ii) donepezil or rivastigmine or galantamine, or pharmaceutically acceptable salts thereof, or any combination thereof, and (iii) one or more pharmaceutically acceptable excipients for the manufacture of a medicament for treating one or more mental, behavioral, or cognitive disorder, such as Alzheimer's disease, vascular dementia, Parkinson's disease, Huntington's disease, or any combination thereof.

In some embodiments of this invention, the pharmaceutically acceptable salt of azelastine in the pharmaceutical composition is azelastine hydrochloride and the pharmaceutically acceptable salt of donepezil or rivastigmine or galantamine in this pharmaceutical composition is donepezil hydrochloride or rivastigmine tartrate or galantamine hydrobromide.

In some embodiments of this invention, azelastine hydrochloride (and/or other salt thereof) in the pharmaceutical composition is provided in an amount of about 4 mg to about 20 mg, and donepezil hydrochloride (and/or other salt thereof) in an amount of about 1 mg to about 4 mg, and/or rivastigmine tartrate (and/or other salt thereof) in an amount of about 1 mg to about 2 mg, and/or galantamine hydrobromide (and/or other salt thereof) in an amount of about 1 mg to about 3 mg. Preferred are compositions formulated to deliver azelastine or a salt thereof in an amount of up to about 20 mg per day (such as from about 1-20 mg, or 2-19 mg, or 3-18 mg, or 4-17 mg, or 5-15 mg, or 6-12 mg, or 8-10 mg, or 3-11 mg, or 2-13 mg, or 7-16 mg, and so on), and donepezil or a salt thereof in an amount of up to about 23 mg per day (such as from about 1-23 mg, or 2-22 mg, or 3-20 mg, or 4-18 mg, or 5-16 mg, or 6-15 mg, or 7-12 mg, or 1.5-3 mg, or 1-2 mg, or 2.5-5 mg, and so on) and/or an amount of rivastigmine or a salt thereof in an amount of up to about 9.5 mg per day (such as from about 1-9.5 mg, or 2-9 mg, or 3-8 mg, or 4-7 mg, or 5-6 mg, or 3.5-8.5 mg, or 2.5-7.5 mg, and so on) and/or an amount of galantamine or a salt thereof in an amount of up to about 24 mg per day (such as from about 1-24 mg, or 2-22 mg, or 3-20 mg, or 4-18 mg, or 5-16 mg, or 6-15 mg, or 7-12 mg, or 8-10 mg, or 0.5-2 mg, or 0.8-2.8 mg, or 1-1.5 mg, or 1.2-2.5 mg, and so on). Depending on the application, higher amounts of any one or more of these could be used in certain embodiments.

The present invention also includes an oral pharmaceutical dosage form of the pharmaceutical composition that is a solid form or a liquid form.

The present invention further includes the medical use of the oral pharmaceutical dosage form of the pharmaceutical composition through administration of the dosage form to patients with a neurodegenerative disorder such as Alzheimer's disease, vascular dementia, or Parkinson's disease.

In some embodiments of this invention, an oral pharmaceutical dosage form of the pharmaceutical composition containing azelastine hydrochloride (and/or other salt thereof) in an amount of about 8 mg to about 12 mg and donepezil hydrochloride in an amount of about 1 mg to about 4 mg or rivastigmine tartrate in an amount of about 1 mg to about 2 mg or galantamine hydrobromide in an amount of about 1 mg to about 3 mg is administered to patients with middle to late stage Alzheimer's disease. In embodiments, any of the ranges disclosed herein relating to any of the components of the composition can be formulated as an oral dosage, such as a solid, liquid, gel, or solution.

DETAILED DESCRIPTION OF THE INVENTION

The inventors of the present invention surprisingly found that a pharmaceutical composition with an oral dosage form comprising the active agents, a salt form of azelastine and a salt form of donepezil or rivastigmine or galantamine, is suitable for treating patients suffering from mental, behavioral, cognitive disorders.

The detailed description provided below is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

Definitions

As used in the present specification, the following words and phrases are generally intended to have the meanings as set forth below, except to the extent that the context in which they are used indicates otherwise.

Mental, behavioral, cognitive disorders can include but are not limited to Alzheimer's disease, dementia, Parkinson's disease, Huntington's disease and combinations of any thereof and other neurodegenerative disorders.

As used herein, the term "donepezil" refers to donepezil free base, 2,3-dihydro-5,6-dimethoxy-2-[[1-(phenylmethyl)-4-piperidinyl]methyl]-1H-inden-1-one. In certain embodiments, donepezil also includes any pharmaceutically acceptable salt, such as the hydrochloride or HCl salt. Preferably, in any embodiments of the invention as described herein, the donepezil is in the form of its hydrochloride salt, as donepezil hydrochloride or donepezil HCl. More preferably, in any embodiment of the invention as described herein, reference to the amounts and dosage ranges of donepezil in oral dosage forms are to the amounts and dosage ranges of donepezil hydrochloride.

As used herein, the term "rivastigmine" refers to rivastigmine free base, (S)-3-(1-(dimethylamino)ethyl)phenyl ethyl (methyl)carbamate. In certain embodiments, rivastigmine also includes any pharmaceutically acceptable salt, such as the tartrate salt. Preferably, in any embodiments of the invention as described herein, the rivastigmine is in the form of its tartrate salt, as rivastigmine tartrate. More preferably, in any embodiment of the invention as described herein, reference to the amounts and dosage ranges of rivastigmine in oral dosage forms are to the amounts and dosage ranges of rivastigmine tartrate.

As used herein, the term "galantamine" refers to galantamine free base, (4aS,6R,8aS)-5,6,9,10,11,12-Hexahydro-3-methoxy-11-methyl-4aH-[1]benzofuro[3a,3,2-ef][2]benzazepin-6-ol. In certain embodiments, galantamine also includes any pharmaceutically acceptable salt, such as the hydrobromide salt. Preferably, in any embodiments of the invention as described herein, the galantamine is in the form of its hydrobromide salt, as galantamine hydrobromide or galantamine HBr. More preferably, in any embodiment of the invention as described herein, reference to the amounts and dosage ranges of galantamine in oral dosage forms are to the amounts and dosage ranges of galantamine hydrobromide.

As used herein, the term "azelastine" refers to azelastine free base, or 4-(p-Chlorobenzyl)-2-(hexahydro-1-methyl-1H-azepin-4-yl)-1-(2H)-phthalazinone. In certain embodiments, azelastine also includes any pharmaceutically acceptable salt, such as the hydrochloride or HCl salt. Preferably, in any embodiments of the invention as described herein, azelastine is in the form of its hydrochloride salt, as azelastine hydrochloride or azelastine HCl. More preferably, in any embodiment of the invention as described herein, reference to the amounts and dosage ranges of azelastine in the solid oral dosage forms are to the amounts and dosage ranges of azelastine hydrochloride.

As used herein, "treating" or "treatment" means complete cure or incomplete cure, or it means that the symptoms of the underlying disease or associated conditions are at least reduced and/or delayed, and/or that one or more of the underlying cellular, physiological, or biochemical causes or mechanisms causing the symptoms are reduced, delayed and/or eliminated. It is understood that reduced or delayed, as used in this context, means relative to the state of the untreated disease, including the molecular state of the untreated disease, not just the physiological state of the untreated disease.

The term "effective amount" refers to an amount that is sufficient to effect treatment, as defined below, when administered to a mammal in need of such treatment. The therapeutically effective amount will vary depending upon the patient being treated, the weight and age of the patient, the severity of the disease condition, the manner of administration and the like, which can readily be determined by one of ordinary skill in the art. The pharmaceutical compositions may be administered in either single or multiple doses by oral administration. Administration may be via capsule, tablet, or the like.

The term "about" used herein in the context of quantitative measurements means the indicated amount ±10%. For example, with a ±10% range, "about 5 mg" can mean 4.5-5.5 mg.

The pharmaceutical composition may be formulated for pharmaceutical use using methods known in the art, for example, Ansel's Pharmaceutical Dosage Forms and Drug Delivery Systems Tenth (by Loyd Allen, 2013) and Handbook of Pharmaceutical Manufacturing Formulations (Volumes 1-6 by Sarfaraz K. Niazi). Accordingly, incorporation of the active compounds and a controlled, or slow release matrix may be implemented.

Either fluid or solid unit dosage forms can be readily prepared for oral administration. For example, admixed with conventional ingredients such as dicalcium phosphate, magnesium aluminum silicate, magnesium stearate, calcium sulfate, starch, talc, lactose, acacia, methyl cellulose and functionally similar materials as pharmaceutical excipients or carriers. A sustained release formulation may optionally be used. In older or incoherent subjects sustained release formulations may even be preferred. Capsules may be formulated by mixing the compound with a pharmaceutical diluent which is inert and inserting this mixture into a hard gelatin capsule having the appropriate size. If soft capsules are desired, a slurry of the compound with an acceptable vegetable, light petroleum or other inert oil can be encapsulated by forming into a gelatin capsule.

Suspensions, syrups and elixirs may be used for oral administration or fluid unit dosage forms. A fluid preparation including oil may be used for oil soluble forms. A vegetable oil such as corn oil, peanut oil or a flower oil, for example, together with flavoring agents, sweeteners and any preservatives produces an acceptable fluid preparation. A surfactant may be added to water to form a syrup for fluid unit dosages. Hydro-alcoholic pharmaceutical preparations may be used having an acceptable sweetener, such as sugar, saccharin or a biological sweetener and a flavoring agent in the form of an elixir.

The solid oral dosage formulation of this disclosure means a form of tablets, caplets, bi-layer tablets, film-coated tablets, pills, capsules, or the like. Tablets in accordance with this disclosure can be prepared by any mixing and tableting techniques that are well known in the pharmaceutical formulation industry. In some examples, the dosage formulation is fabricated by direct compressing the respectively prepared sustained-release portion and the immediate-release portion by punches and dies fitted to a rotary tableting press, ejection or compression molding or granulation followed by compression.

The pharmaceutical compositions provided in accordance with the present disclosure are usually administered orally. This disclosure therefore provides pharmaceutical compositions that comprise a solid dispersion comprising azelastine and donepezil or rivastigmine or galantamine as described herein and one or more pharmaceutically acceptable excipients or carriers including but not limited to, inert solid diluents and fillers, diluents, including sterile aqueous solution and various organic solvents, permeation enhancers, solubilizers, disintegrants, lubricants, binders, glidants, adjuvants, and combinations thereof. Such compositions are prepared in a manner well known in the pharmaceutical arts (see, e.g., Ansel's Pharmaceutical Dosage Forms and Drug Delivery Systems, Tenth (by Loyd Allen, 2013) and Handbook of Pharmaceutical Manufacturing Formulations (Volumes 1-6 by Sarfaraz K. Niazi)).

The pharmaceutical composition may further comprise pharmaceutical excipients such as diluents, binders, fillers, glidants, disintegrants, lubricants, solubilizers, and combinations thereof. Some examples of suitable excipients are described herein. When the pharmaceutical composition is formulated into a tablet, the tablet may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

In embodiments, the pharmaceutical composition can comprise a) about 4 mg-20 mg of azelastine HCl (or other salt thereof) and b) about 1 mg to 4 mg of donepezil HCl or about 1 mg to 2 mg rivastigmine tartrate or about 1 mg to 3 mg galantamine HBr or a) about 8 mg-16 mg of azelastine HCl (or other salt thereof) and b) about 1 mg to 4 mg of donepezil HCl or about 1 mg to 2 mg rivastigmine tartrate or about 1 mg to 3 mg galantamine HBr or a) about 10 mg-14 mg of azelastine HCl (or other salt thereof) and b) about 1 mg to 4 mg of donepezil HCl or about 1 mg to 2 mg rivastigmine tartrate or about 1 mg to 3 mg galantamine HBr. For example, the composition can comprise a) about 12 mg of azelastine HCl and b) about 4 mg of donepezil HCl or about 2 mg of rivastigmine tartrate or about 3 mg of galantamine HBr. Further, for example, compositions of the invention can comprise azelastine or a pharmaceutically acceptable salt of azelastine present in an amount in the range of about 4 mg to about 50 mg and donepezil HCl in an amount in the range of about 1 mg to about 4 mg or rivastigmine tartrate in an amount in the range of about 1 mg to about 2 mg or galantamine HBr in an amount in the range of about 1 mg to about 3 mg. In embodiments, the amount of azelastine HCl (or other salt thereof) present in the composition can be equal to, more than, or less than the amount of donepezil HCl or rivastigmine tartrate or galantamine HBr (or other salt thereof) present in the composition. In embodiments, the amount of azelastine HCl (and/or other salt thereof) present in the composition can be 2 times as much, or 3 times as much, or 4, 5, 6, 7, 8, 9, 10, 15, 20, 25, 30, 35, 40, 45, or 50 times as much as the amount of donepezil HCl or rivastigmine tartrate or galantamine HBr (and/or other salt thereof) present in the composition, or vice versa. Any one or more of the compositions of the invention can be used with any one or more the methods of the invention disclosed herein, or other methods of using the compositions.

It will be understood, that the amount of the pharmaceutical composition containing azelastine HCl and donepezil HCl or rivastigmine tartrate or galantamine HBr actually administered usually will be determined by a physician, in the light of the relevant circumstances, including the condition to be treated, the chosen route of administration, the actual compound administered and its relative activity, the age, weight and response of the individual patient, the severity of the patient's symptoms, and the like.

The pharmaceutical compositions, pharmaceutical dosage forms, and tablets containing azelastine HCl and donepezil HCl or rivastigmine tartrate or galantamine HBr as described herein are administered to a patient suffering from a neurodegenerative disorder, such as Alzheimer's disease, by oral administration once daily, twice daily, once every other day, two times a week, three times a week, four times a week, or five times a week.

In embodiments, patients are administered with the pharmaceutical composition with a therapeutic effective daily dosage of azelastine HCl in the range of 8 mg to about 16 mg and donepezil HCl in an amount in the range of about 1 mg to about 4 mg or rivastigmine tartrate in an amount in the range of about 1 mg to about 2 mg or galantamine HBr in an amount in the range of about 1 mg to about 3 mg.

In embodiments, the pharmaceutical dosage forms and tablets of pharmaceutical compositions containing azelastine HCl and donepezil HCl or rivastigmine tartrate or galantamine HBr as described herein are effective in reversing symptoms in patients with Alzheimer's disease in about 6-24 weeks.

The pharmaceutical composition's therapeutic effectiveness on patients with AD is evaluated by improvements on scores of Mini-Mental State Examination (MMSE) and 12 Neuropsychiatric Inventory-Questionnaires (NPI-Q) having severity scores of 0-3 and distress scores of 0-5.

For treatment of AD, as one of acetylcholinesterase inhibitors, donepezil alone improves MMSE by 9.2% and NPI total by 40.9% and NPI distress by 41.5%.

The following Examples are illustrative and should not be interpreted to limit the scope of the claimed subject matter.

Example 1

10 Patients who are diagnosed with late stage Alzheimer's disease with MMSE scores ranging from 10-1 and NPI-Q having severity scores of 3 and distress scores of 4 or 5 are treated with tablet forms of the pharmaceutical composition containing 12 mg of azelastine HCl and 3 mg of donepezil HCl once daily. After 12 weeks, the MMSE scores of these 10 patients would be expected to increase by at least 9 to range of 20-10, which is 1 to 9 times of improvement in MMSE scores, and their NPI-Q would be expected to have severity scores of 1 and distress scores of for 2, which is 2.5 to 4 times of improvement.

REFERENCES

Bartus R T, Dean R L 3rd, Beer B, et al. 1982. The cholinergic hypothesis of geriatric memory dysfunction. Science, 217:408-17.

Cacabelos R, 2005 Pharmacogenomics and therapeutic prospects in Alzheimer's disease. Exp. Opin. Pharmacother, 6:1967-87.

Cacabelos R, 2005. Pharmacogenomics, nutrigenomics and therapeutic optimization in Alzheimer's disease. Aging Health, 1:303-48.

Cacabelos R, Takeda M. 2006. Pharmacogenomics, nutrigenomics and future therapeutics in Alzheimer's disease. Drugs Future, 31 (Suppl B):5-146.

Clegg A, Bryant J, Nicholson T, et al. 2001. Clinical and cost-effectiveness of donepezil, rivastigmine and galantamine for Alzheimer's disease: a rapid and systematic review. Health Technol Assess, 5:1-137.

Giacobini E. 2006. Cholinesterases in human brain: the effect of cholinesterase inhibitors on Alzheimer's disease and related disorders. In Giacobini E, Pepeu G (eds). The Brain Cholinergic System in Health and Disease. Oxon: Informa Healthcare. p 235-264.

Goedert M, Spillantini MG. 2006. A century of Alzheimer's disease. Science, 314:777-81.

Loveman E, Green C, Kirby J, et al. 2006. The clinical and cost-effectiveness of donepezil, rivastigmine, galantamine and memantine for Alzheimer's disease. Health Technol Assess, 10:1-176.

Lanctôt K L, Herrmann N, Yau K K, et al. 2003. Efficacy and safety of cholinesterase inhibitors in Alzheimer's disease: a meta-analysis. CMAJ, 169:557-64.

Hogan D B, Goldlist B, Naglie G, et al. 2004. Comparison studies of cholinesterase inhibitors for Alzheimer's disease. Lancet Neurol, 3:622-628.

Sugimoto H, Ogura H, Arai Y, et al. 2002. Research and development of donepezil hydrochloride, a new type of acetylcholinesterase inhibitor. Jpn J Pharmacol, 89:7-20.

Whitehouse P, Price D L, Strubel R G, et al. 1982. Alzheimer's disease and senile dementia: loss of neurons in the basal forebrain. Science, 215:1237-9.

Gelosa P, Colazzo F, Tremoli E, Sironi L, Castiglioni L. Cysteinyl Leukotrienes as Potential Pharmacological Targets for Cerebral Diseases. Mediators Inflamm. 2017 May 10.

Alzheimer's Disease International, "World Alzheimer Report 2010: the global economic impact of dementia."

National Institute for Clinical Excellence (NICE), "Donepezil, galantamine, rivastigmine and memantine for the treatment of Alzheimer's disease," NICE Technology Appraisal Guidance 217, National Institute for Clinical Excellence, London, UK, 2011, R. S. Doody, J. K. Dunn, C. M. Clark et al., "Chronic donepezil treatment is associated with slowed cognitive decline in Alzheimer's disease," Dementia and Geriatric Cognitive Disorders, vol. 12, no. 4, pp. 295-300, 2001.

A. Clegg, J. Bryant, T. Nicholson et al., "Clinical and cost-effectiveness of donepezil, rivastigmine and galantamine for Alzheimer's disease: a rapid and systematic review," Health Technology Assessment, vol. 5, no. 1, pp. 1-137, 2001.

R. A. Hansen, G. Gartlehner, A. P. Webb, L. C. Morgan, C. G. Moore, and D. E. Jonas, "Efficacy and safety of donepezil, galantamine, and rivastigmine for the treatment of Alzheimer's disease: a systematic review and meta-analysis," Clinical Interventions in Aging, vol. 3, no. 2, pp. 211-225, 2008.

D. D. Christensen, "Higher-dose (23 mg/day) donepezil formulation for the treatment of patients with moderate-to-severe Alzheimer's disease," Postgraduate Medicine, vol. 124, no. 6, pp. 110-116, 2012.

J. L. Cummings, D. Geldmacher, M. Farlow, M. Sabbagh, D. Christensen, and P. Betz, "High-dose donepezil (23 mg/day) for the treatment of moderate and severe Alzheimer's disease: drug profile and clinical guidelines," CNS Neuroscience & Therapeutics, vol. 19, no. 5, pp. 294-301, 2013.

S. Ferris, J. Cummings, D. Christensen et al., "Effects of donepezil 23 mg on Severe Impairment Battery domains in patients with moderate-to-severe Alzheimer's disease: evaluating the impact of baseline severity," Alzheimer's Research & Therapy, vol. 5, no. 1, article 12, 2013.

M. M. Carrasco, L. Agüera, P. Gil, A. Moriñigo, and T. Leon, "Safety and effectiveness of donepezil on behavioral symptoms in patients with Alzheimer disease," Alzheimer Disease and Associated Disorders, vol. 25, no. 4, pp. 333-340, 2011.

M. R. Farlow, S. Salloway, P. N. Tariot et al., "Effectiveness and tolerability of high-dose (23 mg/d) versus standard-dose (10 mg/d) donepezil in moderate to severe Alzheimer's disease: a 24-week, randomized, double-blind study," Clinical Therapeutics, vol. 32, no. 7, pp. 1234-1251, 2010.

M. Farlow, F. Veloso, M. Moline et al., "Safety and tolerability of donepezil 23 mg in moderate to severe Alzheimer's disease," BMC Neurology, vol. 11, article 57, 2011.

E. Schwam and Y. Xu, "Cognition and function in Alzheimer's disease: Identifying the transitions from moderate to severe disease," Dementia and Geriatric Cognitive Disorders, vol. 29, no. 4, pp. 309-316, 2010.

A. Homma, Y. Imai, H. Tago et al., "Donepezil treatment of patients with severe Alzheimer's disease in a Japanese population: results from a 24-week, double-blind, placebo-controlled, randomized trial," Dementia and Geriatric Cognitive Disorders, vol. 25, no. 5, pp. 399-407, 2008.

S. E. Black, R. Doody, H. Li et al., "Donepezil preserves cognition and global function in patients with severe Alzheimer disease," Neurology, vol. 69, no. 5, pp. 459-469, 2007.

M. R. Farlow, M. L. Miller, and V. Pejovic, "Treatment options in Alzheimer's disease: maximizing benefit, managing expectations," Dementia and Geriatric Cognitive Disorders, vol. 25, no. 5, pp. 408-422, 2008.

A. K. Wallin, N. Andreasen, S. Eriksson et al., "Donepezil in Alzheimer's disease: what to expect after 3 years of treatment in a routine clinical setting," Dementia and Geriatric Cognitive Disorders, vol. 23, no. 3, pp. 150-160, 2007.

D. Galasko, F. Schmitt, R. Thomas, S. Jin, D. Bennett, and S. Ferris, "Detailed assessment of activities of daily living in moderate to severe Alzheimer's disease," Journal of the International Neuropsychological Society, vol. 11, no. 4, pp. 446-453, 2005.

D. Wilkinson, R. Schindler, E. Schwam et al., "Effectiveness of donepezil in reducing clinical worsening in patients with mild-to-moderate Alzheimer's disease," Dementia and Geriatric Cognitive Disorders, vol. 28, no. 3, pp. 244-251, 2009.

M. Bond, G. Rogers, J. Peters et al., "The effectiveness and cost effectiveness of donepezil, galantamine, rivastigmine and memantine for the treatment of Alzheimer's disease: a systematic review and economic model," NIHR HTA Programme Project Number 09/87/01, National Institute for Clinical Excellence, London, UK, 2010.

A. Atri, L. W. Shaughnessy, J. J. Locascio, and J. H. Growdon, "Long-term course and effectiveness of combination therapy in Alzheimer disease," Alzheimer Disease and Associated Disorders, vol. 22, no. 3, pp. 209-221, 2008.

A. Atri, S. D. Rountree, O. L. Lopez, and R. S. Doody, "Validity, significance, strengths, limitations, and evidentiary value of real-world clinical data for combination therapy in Alzheimer's disease: comparison of efficacy and effectiveness studies," Neurodegenerative Diseases, vol. 10, no. 1-4, pp. 170-174, 2012.

C. W. Zhu and M. Sano, "Economic considerations in the management of Alzheimer's disease," Clinical interventions in aging, vol. 1, no. 2, pp. 143-154, 2006.

Epstein A B, van Hoven P T, Kaufman A, Carr W W. Management of allergic conjunctivitis: An evaluation of the perceived comfort and therapeutic efficacy of olopatadine 0.2% and azelastine 0.05% from two prospective studies. Clin Ophthalmol. 2009; 3:329-336.

Bielory L, Bielory B. Ocular allergy: An allergist's perspective. Aug. 16, 2010.

Pflugfelder S C. Prevalence, burden, and pharmacoeconomics of dry eye disease. Am J Manag Care. 2008; 14 Suppl 3:S102-S106.

Bielory L, Lien K W, Bigelsen S. Efficacy and tolerability of newer antihistamines in the treatment of allergic conjunctivitis. Drugs. 2005; 65:215-218.

Bielory L, Buddiga P, Bigelsen S. Ocular allergy treatment comparisons: Azelastine and olopatadine. Curr Allergy Asthma Rep. 2004; 4:320-325.

Baudouin C. Detrimental effect of preservative in eye drops: Implications for the treatment of glaucoma. Acta Ophthalmologica. 2008; 86:716-726.

Lee J S, Lee J E, Kim N, Oum B S. Comparison of the conjunctival toxicity of topical ocular antiallergic agents. J Ocul Pharmacol Ther. 2008; 24:557-562.

Lambiase A, Micera A, Bonini S. Multiple action agents and the eye: Do they really stabilize mast cells? Curr Opin Allergy Clin Immunol. 2009; 9:454-465.

Casale T. The interaction of azelastine with human lung histamine H1, beta, and muscarinic receptor-binding sites. J Allergy Clin Immunol. 1989; 83:771-776.

Hazama H, Nakajima T, Hisada T, Hamada E, Omata M, Kurachi Y. Effects of azelastine on membrane currents in tracheal smooth muscle cells isolated from the guinea-pig. Eur J Pharmacol. 1994; 259: 143-150.

Perhach J L, Connell J T, Kemp J P. Treatment of upper and lower airway disease with azelastine. N Engl Reg Allergy Proc. 1987; 8:121-124.

Szelenyi I, Achterrath-Tuckermann U, Schmidt J, Minker E, Paegelow I, Werner H. Azelastine: A multifaceted drug for asthma therapy. Agents Actions Suppl. 1991; 34:295-311.

Galatowicz G, Ajayi Y, Stern M E, Calder V L. Ocular antiallergic compounds selectively inhibit human mast cell cytokines in vitro and conjunctival cell infiltration in vivo. Clin Exp Allergy. 2007; 37:1648-1656.

Ciprandi G, Pronzato C, Passalacqua G, et al. Topical azelastine reduces eosinophil activation and intercellular adhesion molecule-1 expression on nasal epithelial cells: An antiallergic activity. J Allergy Clin Immunol. 1996; 98(6 Pt 1):1088-1096.

Simons F E, Simons K J. Clinical pharmacology of new histamine H1 receptor antagonist. Clin Pharmacokinet. 1999; 36:329-352.

Boada-Rovira M, Brodaty H, et al. Efficacy and safety of donepezil in patients with Alzheimer's disease: results of a global, multinational, clinical experience study. Drugs Aging. 2004; 21(1):43-53.

Holmes C, Wilkinson D, et al. The efficacy of donepezil in the treatment of neuropsychiatric symptoms in Alzheimer disease. Neurology. 2004 Jul. 27; 63(2):214-9.

Loyd Allen, Ansel's Pharmaceutical Dosage Forms and Drug Delivery Systems, Tenth (2013)

Sarfaraz K. Niazi, Handbook of Pharmaceutical Manufacturing Formulations Volumes 1-6.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Any of the methods disclosed herein can be used with any of the compositions disclosed herein or with any other compositions. Likewise, any of the disclosed compositions can be used with any of the methods disclosed herein or with any other methods. Other embodiments of the invention will be apparent to those skilled in the art from consideration of the specification and practice of the invention.

It is noted in particular that where a range of values is provided in this specification, each value between the upper and lower limits of that range, to the tenth of the unit disclosed, is also specifically disclosed. Any smaller range within the ranges disclosed or that can be derived from other endpoints disclosed are also specifically disclosed themselves. The upper and lower limits of disclosed ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A pharmaceutical composition, comprising:
   about 4 mg to 16 mg azelastine or a pharmaceutically acceptable salt thereof;
   donepezil hydrochloride present in an amount in the range of 1 mg to 3 mg;
   and one or more pharmaceutically acceptable excipients.

2. The pharmaceutical composition of claim 1, wherein the azelastine or the pharmaceutically acceptable salt thereof is present in an amount that is 2-15 times as much as the donepezil hydrochloride.

3. The pharmaceutical composition of claim 1, wherein the composition is in the form of a suspension, syrup, elixir, tablet, caplet, pill, capsule, or gel.

4. A pharmaceutical composition comprising:
   about 10 mg to 50 mg azelastine or a pharmaceutically acceptable salt thereof;
   donepezil or a pharmaceutically acceptable salt thereof, rivastigmine or a pharmaceutically acceptable salt thereof, or galantamine or a pharmaceutically acceptable salt thereof, or any combination thereof;
   and one or more pharmaceutically acceptable excipients.

5. The pharmaceutical composition of claim 4, wherein the donepezil or the pharmaceutically acceptable salt thereof is present in an amount in the range of about 1 mg to about 4 mg; and/or the rivastigmine or the pharmaceutically acceptable salt thereof is present in an amount in the range of about 1 mg to about 2 mg; or the galantamine or the pharmaceutically acceptable salt thereof is present in an amount in the range of about 1 mg to about 3 mg.

6. The pharmaceutical composition of claim 2, wherein the pharmaceutically acceptable salt of azelastine is azelastine hydrochloride.

7. The pharmaceutical composition of claim 4, wherein the pharmaceutically acceptable salt of donepezil is donepezil hydrochloride, the pharmaceutically acceptable salt of rivastigmine is rivastigmine tartrate, or the pharmaceutically acceptable salt of galantamine is galantamine hydrobromide.

8. The pharmaceutical composition of claim 1, wherein the pharmaceutical composition is formulated as an oral pharmaceutical dosage form.

9. The pharmaceutical composition of claim 8, wherein the oral pharmaceutical dosage form is a solid form or a liquid form.

10. A method comprising:
    administering a pharmaceutical composition to a patient having Parkinson's or Huntington's disease, the pharmaceutical composition comprising:
    azelastine or a pharmaceutically acceptable salt of azelastine;

donepezil or a pharmaceutically acceptable salt thereof, rivastigmine or a pharmaceutically acceptable salt thereof, or galantamine or a pharmaceutically acceptable salt of thereof, or any combination thereof; and one or more pharmaceutically acceptable excipients.

11. The method of claim 10, wherein the pharmaceutical composition is administered once or twice a day or once every 2 or 3 or 4 days to the patient in an oral solid or liquid form.

12. The method of claim 10, wherein the azelastine or the pharmaceutically acceptable salt of azelastine is administered to the patient in an amount of up to about 50 mg daily.

13. The method of claim 10, wherein the pharmaceutical composition is administered to the patient for a period of about 6-24 weeks.

14. The method of claim 10, wherein the pharmaceutical composition is administered for a period of time to improve one or more symptoms of the patient's Parkinson's or Huntington's disease.

15. The method of claim 10, wherein the azelastine or the pharmaceutically salt thereof is present in the pharmaceutical composition in an amount that is 2-50 times as much as the donepezil or the pharmaceutically acceptable salt thereof, rivastigmine or the pharmaceutically acceptable salt thereof, or galantamine or the pharmaceutically acceptable salt thereof.

16. The method of claim 10, wherein the pharmaceutical composition is administered by way of sustained release.

17. The method of claim 10, wherein the pharmaceutical composition is administered according to a protocol sufficient to improve one or more symptoms of dementia of the patient chosen from awareness, memory, language, speech, reasoning, mobility, or time arrangement skills of the patient, or combinations thereof.

18. The method of claim 10, wherein the pharmaceutical composition is administered according to a protocol sufficient to improve one or more symptoms of the patient's Huntington's disease chosen from motor skills, cognition skills, or behavior, or combinations.

* * * * *